128/660

United States Patent [19]

Gardineer et al.

[11] Patent Number: 4,508,122

[45] Date of Patent: Apr. 2, 1985

[54] ULTRASONIC SCANNING APPARATUS AND TECHNIQUES

[75] Inventors: Bayard Gardineer, Skillman; David Vilkomerson, Princeton, both of N.J.

[73] Assignee: Ultramed, Inc., Princeton, N.J.

[21] Appl. No.: 443,488

[22] Filed: Nov. 22, 1982

[51] Int. Cl.[3] .......... A61B 10/00

[52] U.S. Cl. .......... 128/660; 73/620

[58] Field of Search .......... 128/660–661; 73/618–626, 633, 641

[56] References Cited

U.S. PATENT DOCUMENTS

| | | | |
|---|---|---|---|
| 3,028,752 | 4/1962 | Bacon | 73/623 X |
| 3,121,324 | 2/1964 | Cowan | 73/622 X |
| 3,163,784 | 12/1964 | Renaut | 73/624 X |
| 4,089,227 | 5/1978 | Falgari et al. | 73/622 |
| 4,248,090 | 2/1981 | Glenn | 73/620 |
| 4,274,421 | 6/1981 | Dory | 73/620 X |
| 4,315,435 | 2/1982 | Proridian | 128/660 X |
| 4,433,690 | 2/1984 | Green et al. | 128/660 |

*Primary Examiner*—Lee S. Cohen
*Assistant Examiner*—Francis J. Jaworski
*Attorney, Agent, or Firm*—Arthur L. Plevy

[57] ABSTRACT

There is disclosed an ultrasonic scanning apparatus for directing ultrasonic energy towards a body under investigation, such as the body of a person. The scanning apparatus consists of a focussed ultrasonic transducer which is capable of radiating a beam of ultrasonic energy in a given direction. The beam emanating from the transducer impinges upon at least one surface of a rotating reflector where the rotating reflector directs the beam relatively perpendicular to the direction of the beam as propagated from the transducer. The redirected beam can then be further focussed or reflected to further shape the beam prior to directing the beam towards the body under investigation.

19 Claims, 12 Drawing Figures

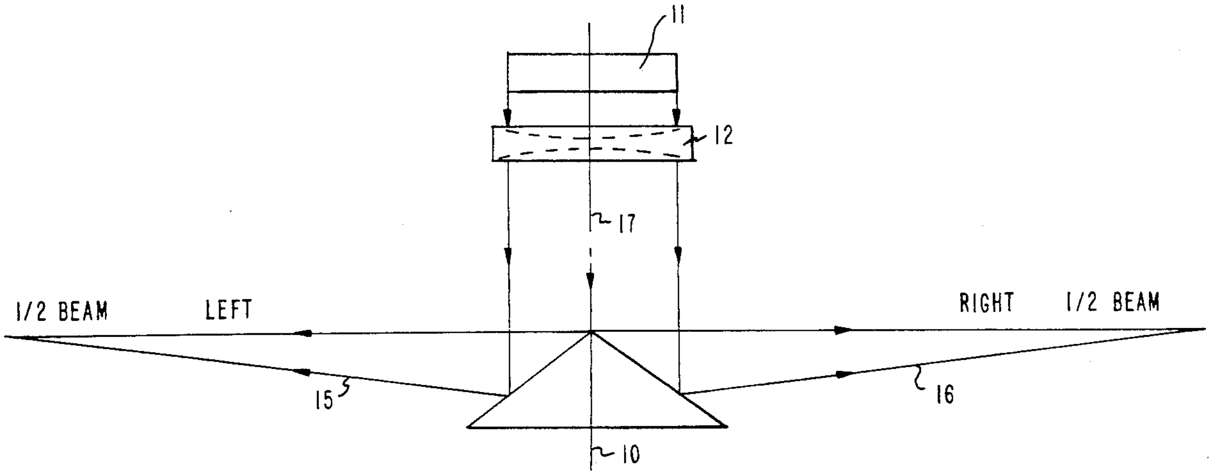
FIG. 1
FIG. 2
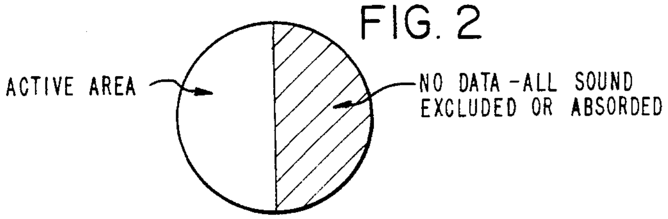
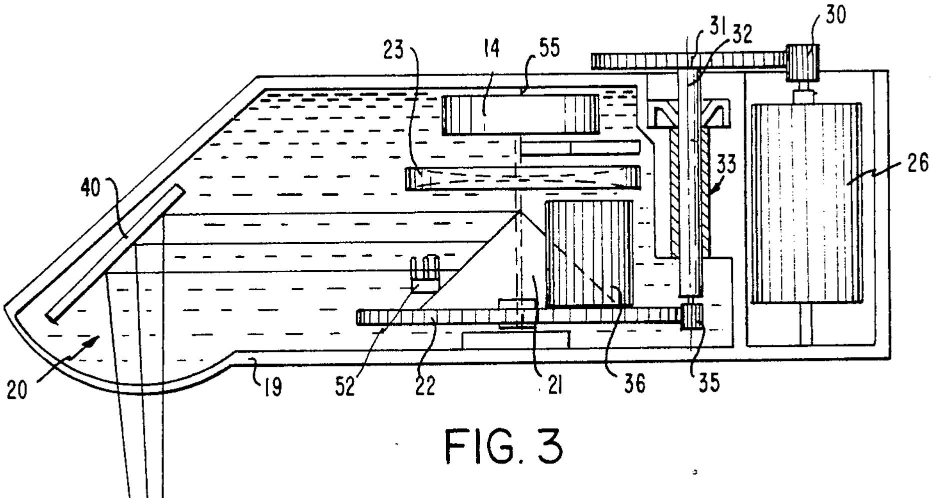
FIG. 3
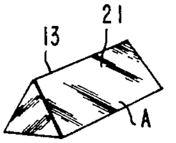
FIG. 3a

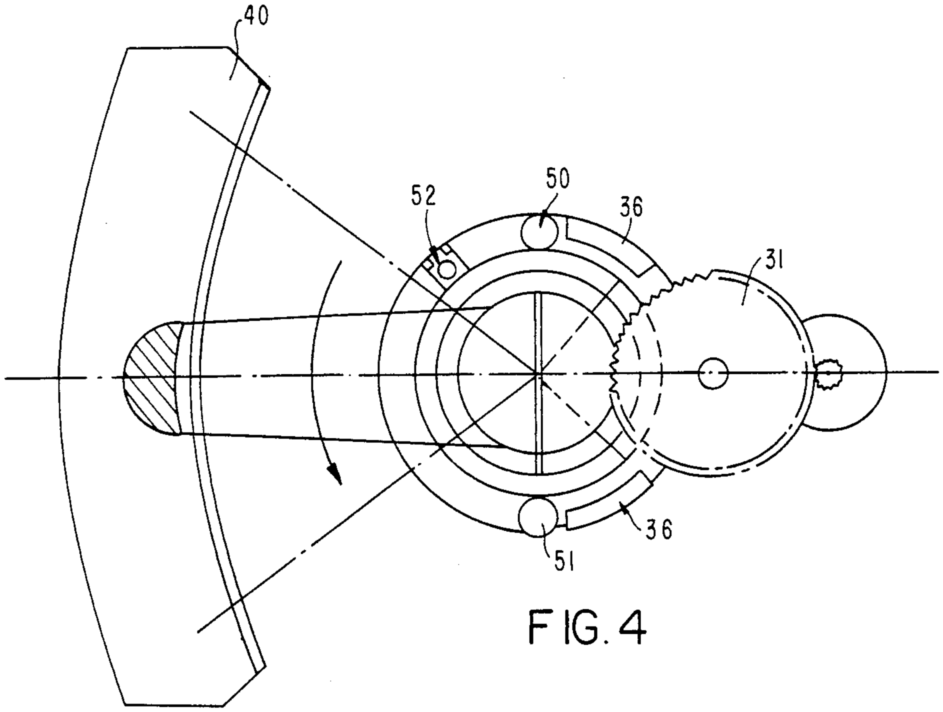
FIG. 4
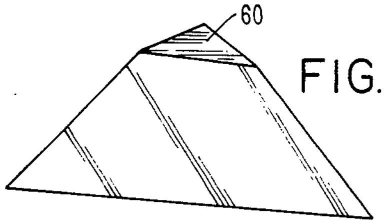
FIG. 5a
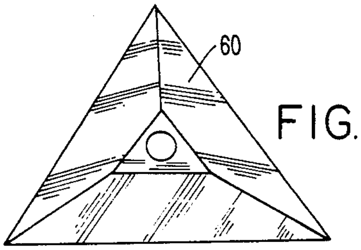
FIG. 5b
FIG. 5c
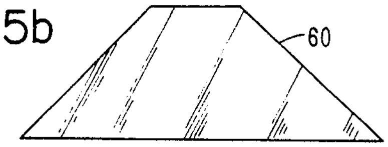
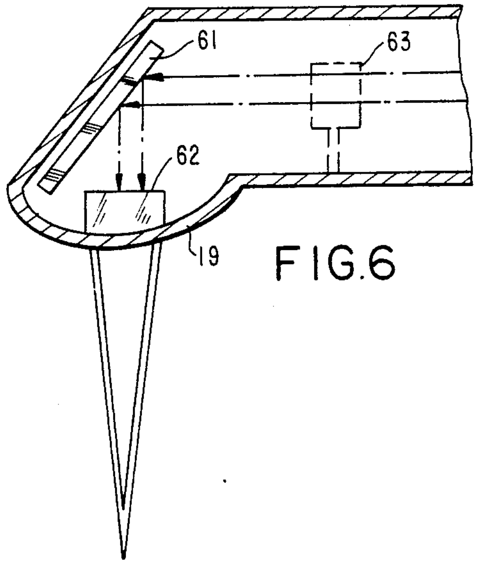
FIG. 6
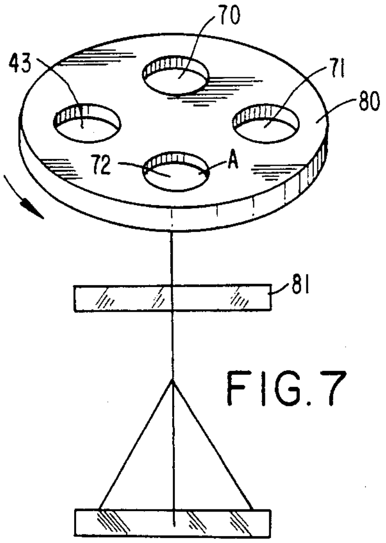
FIG. 7

ULTRASONIC SCANNING APPARATUS AND TECHNIQUES

BACKGROUND OF THE INVENTION

This invention relates to an ultrasonic imaging system in general and in particular to an ultrasound system employing a novel mechanical scanning arrangement.

Ultrasound imaging systems have been widely used in medical applications because such systems permit imaging of internal structures of the body without the use of harmful forms of radiation. In particular the systems have achieved wide spread use in the filed of obstetrics and gynecology. In such systems a series of very short ultrasound pulses are transmitted through a suitable conducting medium such as a fluid as water and are caused to impinge on the object or patient under examination. The returning echos from increasing depth of penetration arrive at the receiver with predetermined time delays with respect to the time of the initial pulse transmissions. These return echos are displayed on a video display such as a CRT in known presentations such as an A, B, or C Scan. The scan presentations provide a television type of image of the interior of the patient. In this manner the physician or practitioner, by viewing the display, can determine the presence of tumors or abnormalities, and thus the display serves as a useful diagnostic tool in rendering medical advice.

In many such systems the scanner is a hand held unit which the physician manually moves about the body of a patient to thereby perform imaging according to a particular ailment or complaint.

It is desirable for hand held scanners utilizing ultrasound to provide as clear a scan picture of the volume of tissue under investigation as is possible. In scanning patients and unborn babies, this is especially true since the fetus can be followed from its early stages only if picture definition and gray scale are acceptable.

Present equipment utilizes either a phased array or plain arrays to visualize and to implement fetal scans. These type of scanners do not provide as clear an image as is desirable. On the other hand, mechanically scanned units provide a fan-shaped image with resolution that varies from good to poor as the beam penetrates farther into tissue under investigation.

As indicated, the prior art is replete with a number of patents and technical descriptions of typical systems employing ultrasound scanning. U.S. Pat. No. 4,213,344 entitled METHOD AND APPARATUS FOR PROVIDING DYNAMIC FOCUSING AND BEAM STEERING IN AN ULTRASONIC APPARATUS, issued on July 22, 1980 to J. L. Rose. This patent discloses a technique for varying the depth of focus of an ultrasonic system. In the system described a plate is rotated at a uniform speed. The plate is of varying thicknesses which causes the beam to penetrate tissue in different degrees as the plate varies the focal zone length of the ultrasonic beam.

U.S. Pat. No. 4,325,381 entitled ULTRASONIC SCANNING HEAD WITH REDUCED GEOMETRICAL DISTORTION, issued on Apr. 20, 1982 to W. E. Glenn. This patent describes a system which attempts to control and reduce geometric distortion of an ultrasonic scanning beam. In the system described a scanning mirror is nodded to produce oscillatory motion. The system employs an acoustic converging lens to reduce geometric distortion by selecting the focal length of the lens to be approximately equal to the distance between the scanning reflector and an output lens system. In any event, there are a number of other patents which are pertinent to ultrasonic scanning systems and which are indicative of scanning systems employing both phased and plain arrays.

An ideal system which has been considered by the prior art would be a mechanically scanned transducer which would move in straight line with its beam orthogonal to the subject. Such a unit ideally would provide a scan plane which is flat in planar configuration and rectangular in scope from the point of contact with the patient and remains so as the beam penetrates. Such a device would provide a field of view essentially between 10 to 12 centimeters in length and of the order of 20 centimeters in depth. In view of this one can imagine a focused transducer or a transducer with a focusing lens traversing linearly back and forth over the 12 centimeter path at a reasonable rate (say 5 frames per second).

In view of modern construction techniques such a device can be constructed but it would be an extremely difficult and expensive proposition. In regard to such a device the rapid movement of the various structures within the scanning head would set up large vibrational forces that would be difficult to counteract. Apart from this problem, such a transducer would require a two-directional writing of the transducer as it is scanned back and forth and this would be difficult to synchronize so that a display which would be free from shimmy would not be provided.

In accordance with the present invention, a desired scan plane is implemented by means of a rotating or spinning mirror that runs at a constant speed. The mirror to be described may take the shape of a solid triangle or may take the shape of a truncated tetrahedron. The rotating mirrors to be described operate to eliminate the start-stop inertial pertubations found in oscillating scanners. As will be explained, the unit according to this invention writes in one direction only and thereby eliminates the shimmy found in most back and forth systems.

In the system to be described, the ultrasonic beam is split into two beams. A successful mechanically scanned water path scanner has been designed and marketed utilizing a physically split round transducer. In the marketed system each one-half section or D of this transducer has one-half of an acoustic lens in its path, also in a D shape. Thus, each half of the transducer can be employed to provide a separately focussed sonic beam or pulse. This technique has been implemented in commercially available equipment. The lens and the transducer are oscillated back and forth to scan an arcuate zone with each half of the transducer lens set focused at a different depth. The point is that the D-shaped beam can be employed with good resolution provided that it is scanned perpendicular to the straight side of the D. If the beam is scanned parallel to the straight side of the D, the resolution is cut in half.

In this invention, the focused beam is deflected by a solid triangular shaped reflector such as a tent shaped reflector. The reflector of this invention splits the beam into two diametrically opposed beams, each of a D shape. In this manner, as will be explained, the unique reflector according to this invention circumvents many of the problems in the prior art systems and provides excellent resolution utilizing a relatively simple and compact configuration. The basic concepts to be described herein have also been the subject matter of a Disclosure Document filed on May 21, 1982, docket document No. 108454.

BRIEF DESCRIPTION OF THE PREFERRED EMBODIMENT

An ultrasonic scanner apparatus for directing ultrasonic energy towards a body under investigation, comprising a focussed ultrasonic transducer means for radiating a beam of ultrasonic energy in a given direction, a rotating reflector having at least two distinct reflecting surfaces at least one of which intercepts said beam for redirecting the beam in a direction relatively perpendicular to said given direction and means responsive to said redirected beam to direct the same towards said body under investigation.

BRIEF DESCRIPTION OF THE FIGURES

FIG. 1 is a diagrammatic view of a scanning technique employed in this invention.

FIG. 2 is a representation of the scanning pattern employed.

FIG. 3 is a side elevational view of a scanning head according to this invention.

FIG. 3A is a perspective view of a tent shaped reflector according to this invention.

FIG. 4 is a top view of the scanning head of FIG. 3.

FIG. 5A is a perspective view of a truncated tetrahedron which can be employed as an alternate scanning mirror.

FIG. 5B is a top view of the mirror of FIG. 5A.

FIG. 5C is a front view of the mirror of FIG. 5A.

FIG. 6 is a schematic view of a scan head depicting the position of an auxiliary lens.

FIG. 7 is a schematic view of a turret assembly used with this invention for implementing various transducers.

DETAILED DESCRIPTION OF THE FIGURES

Figure 8:
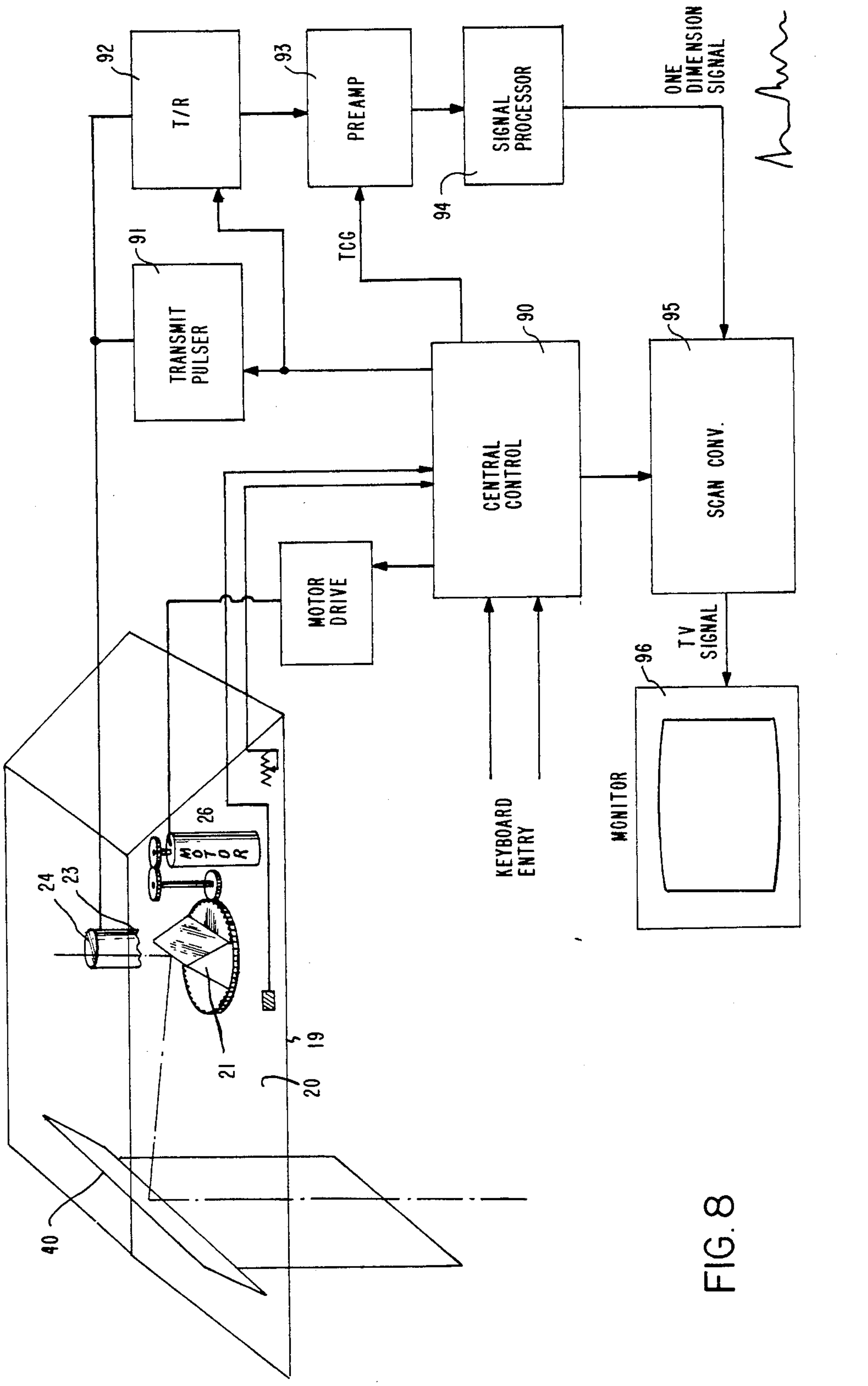
FIG. 8 is a schematic diagram of an ultrasound system employing this invention.

Referring to FIG. 1, there is shown a diagrammatic view showing the reflector operation of the scanning system to be described. Essentially, a reflector 10 is of a solid triangular configuration wherein FIG. 1 shows the front view of the reflector A transducer 11 which is a fixed flat transducer generates ultrasonic radiation when activated. The radiation is focussed through a lens system 12 onto the side surfaces of reflector 10.

As shown in FIG. 1, the energy is reflected to produce a right and a left beam, 15 and 16, each of which is designated as a half beam.

As shown in FIG. 2, one beam is absorbed by the system while the other beam is employed as an active beam to develop data determinative of an ultrasonic scan.

As seen in FIG. 2, if one beam if absorbed, then the transducer employed in the system functions as a D type transducer. As will be explained, the reflector 10 is rotated with the transducer 11 and the lens system being fixed and aligned coaxially with each other and with the reflector 10. As the reflector 10 is rotated, the beam can be scanned in a plane which is essentially perpendicular to the main axis 17. As long as all sound from the unused side of the reflector is suppressed, the transducer will function as a D shaped unit. As the area under use which is the active area shown in FIG. 2 will change with rotation, the D shape is constant and scanning can take place all around the scanning plane.

Referring to FIG. 3, there is shown a side view of a one zone scanning system according to this invention. Essentially, the scanning head is contained in a housing 19. The housing 19 is dimensioned so that it may be hand held and moved by the physician as desired. The housing contains an acoustic liquid 20 which, for example, may be water, castor oil or some other substance which has an index of refraction to match the human body. Located within the housing 19 is a triangular or tent reflector 21.

As shown in FIG. 3A, the reflector 21 is of a tent like configuration. It has a base which is secured to the platform with the base angles of the front triangular cross section being 45 degrees. The apex of the solid triangle faces the transducer 14 with the major surfaces as surface A and B constituting the reflecting surfaces. Above the reflector is a fixed lens system 23. The lens 23 is a concave lens which generally converges ultrasonic energy obtained from the fixed transducer 14. Transducer 14 is designated as a flat transducer and is a piezoelectric device which is available in the prior art. The rotation of the platform 22 is afforded by means of a motor 26 located within the housing 19. The motor has its drive shaft coupled to a gear 30 which in turn rotates a gear 31 coupled to a shaft 32. The shaft 32 is located within a sleeve bearing 33. Coupled to the bottom of the shaft is a gear 35 which drives the platform 22 and therefore the two surfaced reflector 21. Positioned on one side of the reflector is an acoustic absorber 36 which operates to absorb one half beam as beam 16 of FIG. 1.

As seen in FIG. 3 the ultrasonic energy generated in transducer 14 is focussed on the surface of the rotating reflector 21 and directed to a tilted mirror 40 which directs the ultrasonic energy through the housing 19 to a focal point 41.

FIG. 4 depicts a top view of the apparatus shown in FIG. 3. The reflector 40 is a tilted conical reflector where the beam is formed. In order to develop synchronizing signals for the system, the platform 22 has located thereon first and second magnets 50 and 51. As will be explained, the magnets may be located on the same diameter which is aligned with the apex of the tent shaped reflector 21. In the Preferred Embodiment one magnet is offset from the diameter by a selected angle. A Hall Effect device 52 is shown positioned with respect to the platform so that it can respond to the magnetic field generated by each of the magnets during rotation of the platform and reflector. In this manner, the Hall Effect device 52, as will be explained, provides output pulses indicative of the position of the reflector 21 during rotation whereby these signals are employed for motor control and for ascertaining synchronization of the display. The device 52 is positioned near or beneath gear 22 so as not to reflect the ultrasonic beam.

In FIGS. 3 and 4 the beam is again deflected by the reflector 40 to cause the beam to propagate along a path which is parallel to the main axis 55 of the rotating reflector assembly. The shape of the beam, a "D", as it strikes reflector 40 is shown hatched in FIG. 4. The surface of the reflector 40 is a conical surface, and the reflector as shown is tilted at the same angle as the base angle of the reflector 21. The reflector 40 has a curved surface representing a relatively large curve which does not substantially distort the beam wavefront. The scan plane is slightly saddle-like and its boundaries go from about 8 centimeters to about 10 centimeters. This plane gives a good approximation of a flat plane and operates to provide a reasonable scan display.

The reflection surface of the reflector 40 is selected so that the curve is manifested as a tilted paraboloid to form a scan plane of the desired configuration.

Essentially, as shown in FIG. 3, the lens 23 is a fixed lens which is concave. In the system depicted, one may substitute for the fixed lens two lenses which can be interchanged. By using a first lens of a short focal length and a second lens of a long focal length, one can achieve focusing for each lens at a different depth. One can rotate the lens assembly at the same rate as the rotating mirror, the short or long focal length lens providing a two-zone option. The frame rate in this instance is one half the frame rate of the single zone and would require the scan converter to accept and combine the short and the long lens images. Also, either the long focus side of the unit or the near focus side of the unit would be used to fill the whole scan converter. This would cut the scan rate in half as compared to the single lens approach but has the advantage of offering either near or far field views in good focus with less complexity.

As can be seen from FIG. 3, the lens 23 is coaxial about the center line of the rotating reflector 21. To obtain good quality with this structure, the transducer 24 should have a relatively large aperture. Conventional transducers available commercially are about half as large as the transducer required in operation with the structure shown in FIG. 3. Such a transducer as employed in the structure shown in FIG. 3 has a diameter of about 1 inch. In any event, commercial transducers which are relatively inexpensive are typically one-half inch in diameter. Therefore, in using this structure, one can mount a smaller transducer with a lens to one side of the tent reflector 21 and thus mount the transducer off axis so that the entire beam falls only on one side of the reflector. This configuration will tend to alter the path of the beam somewhat, but this can be compensated for by conventional techniques such as an alteration in reflector 40 or the use of a variable delay line at the input to the scan converter. By offsetting the transducer, one can then employ inexpensive and typically available transducers and still provide a hand held scanner that operates according to the above described conditions.

In regard to the above noted discussion, the tent shaped mirror basically exhibits two reflecting surfaces.

Referring to FIGS. 5A and 5C, there is shown a reflecting mirror 60 of a truncated tetrahedron configuration. As can be ascertained from the top view of FIG. 5B, the tetrahedron 60 has three reflecting surfaces. This reflecting device 60 would be mounted on the platform 22 as shown in FIG. 3. By using a truncated tetrahedron, one increases the active pulsing time of the system which is the proportion of time that a reflecting surface is pointed towards the stationary mirror 40. Increasing the number of reflecting sides, increases the active time in proportion for the tetrahedron 60. This is an increase by a ratio of 3 to 2. In any event, the area of the reflecting surface is reduced. In order to determine whether a three-sided rotating mirror or one with a larger number of sides is desirable depends upon the design trade-offs of increased frame rate with increasing number of sides. These trade-offs have to be considered in view of the increased complexity in the fabrication of multisided mirrors and the diminished reflection area that results from their use.

In FIGS. 3 and 4 it has been explained that the surface of the stationary mirror 40 determines the path of the scanning beam. Hence in order to provide a particular shape scanning plane, the curve of the stationary mirror as indicated above is formed as a paraboloid whose exact dimensions can be calculated mathmatically to approximate a plane.

Referring to FIG. 6, there is shown a partial view of the scanning housing 19 employing a straight surface mirror 61 which receives the ultrasonic waves from the rotating mirror and then directs the waves through a cylindrical lens 62. The lens 62 operates on the waves to produce the desired rectangular flat field. Thus, in FIG. 6, the auxiliary lens 62 is positioned at the exit window of the scanner. An auxiliary lens 63 (shown dashed in FIG. 6) may also be positioned closer to the rotatable mirror in which case it is a smaller lens but of higher curvature. As is known to those skilled in the art, by changing the focal length of the auxiliary lens as lens 62 or 63, one can vary the geometry of the scan plane. For example, if the focal length of the lens equals the distance to the rotating mirror as lens 63, the resulting scan plane is rectangular. If the focal length is greater, then the scanned plane becomes trapezoidal being narrower closer to the scan head and wider farther away. If the focal length is smaller than the distance to the rotating mirror, the scan beams will converge to a point.

Therefore, as shown in FIG. 6, using an auxiliary lens provides an extra degree of freedom in the scan head design with a relatively minor cost in fabrication and construction.

Referring to FIG. 7, another extremely useful feature of the invention is that the rotating mirror which produces the scan plane allows for an extremely flexible instrument which can employ various transducers which are positioned in the propagation path means of a turret system. As shown in FIG. 7, transducers such as 70, 71, 72 and 73 are positioned on a rotatable turret 80. The turret is indexed so that it may rotate with respect to the lens system 81. Any one of the four transducers, as 70 to 73, can be rotated into position A, presently shown occupied by transducer 72. In this configuration the desired transducer is rotated in position just as is done to obtain the desired objective lens in a multi-objective microscope. A suitable switch connects the signal cable to the transducer. The lens 81 may be used or each transducer may operate with its own lens which may also be positioned on a corresponding turret assembly. In utilizing the turret configuration, one can thereby provide transducers with different frequencies and different focal lengths. As is known, higher frequencies do not penetrate as deeply into the body and such a selective control of the transducer as by utilizing a turret assembly would be quite useful in general purpose ultrasound imaging systems. The typical frequency employed may vary from 1 to 15 mhz, and the transducer structures employed as indicated are piezoelectric substances formed from ceramics or such materials as lithium niobate.

Referring to FIG. 8, there is shown a block diagram of a typical ultrasonic imaging system employing the scan head as above described. In FIG. 8 the same reference numerals have been employed for the scan head as shown in FIG. 3. Essentially, the motor 26 is coupled to a motor drive circuit. The motor drive circuit is of a conventional circuit configuration and many examples are well known in the art. A central control module 90 typically consists of a digital logic circuit or microprocessor of the type presently employed in ultrasonic systems. The control circuit 90 is coupled to a transmitter pulser circuit 91. The pulser produces a short electrical pulse which typically consists of a few cycles of the operating frequencies of 1 to 15 mhz. This pulse, which may also be a voltage spike, is coupled to the transducer 24 to cause the transducer to produce a short pulse of sonic energy at the driving frequency, or in the case of pulse excitation, at the frequency of the transducer resonance. The sonic pulse generated by transducer 24 propagates through the lens 23 down through the liquid coupling medium 20 which may be water and strikes the rotating mirror 21. The angular position of the mirror 21 determines where the pulse strikes the stationary mirror 40 which in turn reflects the pulse downwardly out of the scan head and into the body of the patient. The pulse propagates through the body with smaller reflections which are typically 0.01 percent of the power at each tissue interface encountered.

The pulses reflected from the body retrace the propagation path and enter the scan head and are retraced back to the rotating mirror 21 by the stationary mirror 40. The reflected pulses from the rotating mirror are directed back through the lens 23 to strike the transducer 24. In this system the ultrasound completes the complete round trip in about 300 microseconds, and the rotating mirror is controlled so that it does not rotate appreciably in that length of time. This sets the upper limit on the number of frames per second.

The transducer 24 operates to convert the sonic pulse to an electrical signal. During this time, the transmit pulser 91 is at a high impedance as controlled by the central control unit 90. During the return of the pulse, the transmit/receiver module 92 (T/R) is enabled by the central control. The T/R unit 92 controls a sensitive preamplifier so that the pulse is now amplified. The preamplifier 93 is a low noise, high dynamic range amplifier. The gain of the preamplifier 93 is controlled by module 90 according to well known techniques. The gain is low for early returning echos and increases with time. This compensates for the attenuation suffered by the sonic pulse as it propagates through a longer and longer tissue path with increasing time. The gain control as afforded to the preamplifier 93 by the central control 90 is referred to in the art as time controlled gain or TCG.

As indicated, the technique is well known and the rate of gain controll may be inputed into the control module 90 from a control panel or a suitable program. The signals representing the echos from different tissue interfaces vary greatly in power, typically over 40 decibels (db) or more. Therefore, it is usual in the art to logarithmically compress the signals, video detect and otherwise process the signal to enhance the visibility of the resulting image. These techniques are also well known in the prior art and are performed in the signal processing module 94.

In ultrasound systems, the returning echos from one pulse provides one line of an ultrasonic image. That line in the ultrasonic image corresponds to the sequence of interfaces encountered by the sonic pulse as it propagates downwardly into the body of the patient. The line information is typically stored in a scan converter 95 that assembles the information from the sequence of lines produced as the rotating mirror 21 rotates. The assembled image or frame is in a video format so that it can be displayed directly on a TV monitor 96 or recorded on a video type recorder and so on.

In such systems the length of the image line or how far down the instrument collects the echo information is set by how long the system receives echo returns. At a speed of 1.5 millimeters per microsecond, a 20 centimeter depth of field would require an acquisition time of approximately 267 microseconds. After the echo from the deepest point in the body to be scanned is received, the control module 90 waits for the rotating mirror 21 to move so that the next line can be scanned. When the rotating mirror is in the proper position, typically so that the next scan line is one lines resolution width away from the last, the signal is again initiated by the control module 90 keying or activating the transmit pulser 91. This operation sets the T/R switch 92 into its high impedance state to enable the operation to continue line by line. The scan converter 95 must accurately assemble the lines into an image. The determining factor in the accuracy and stability of the image is the positioning of the scan lines, the angular position of the rotating mirror 21 that establishes the spatial position of these lines. Hence the position of the rotating mirror 21 must be accurately known at all times.

Figure 9:
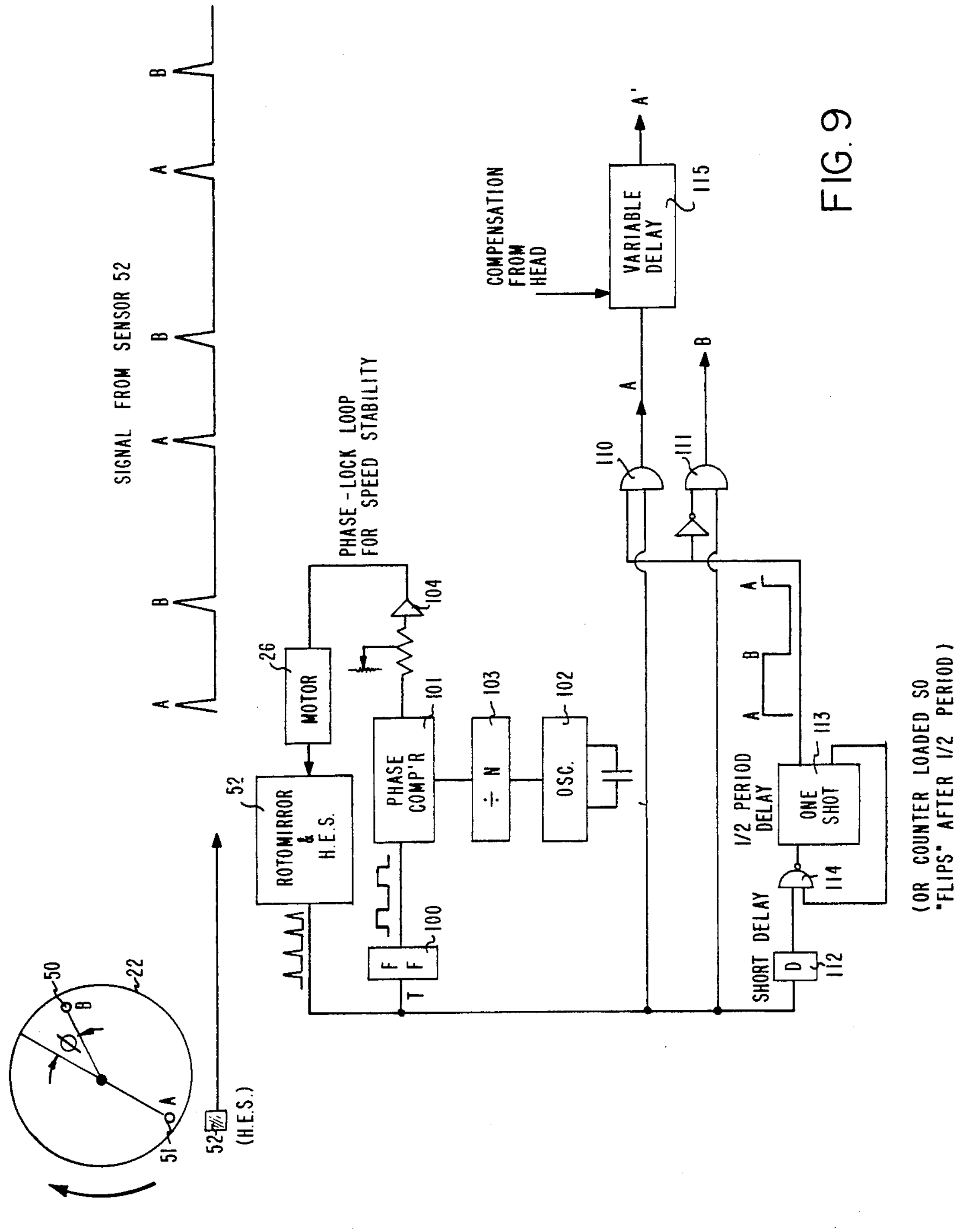
FIG. 9 is a schematic diagram including timing wave forms showing the control for a rotating mirror employed in this invention.

Referring to FIG. 9, as indicated in FIG. 4, the platform 22 to which the base of the rotating mirror is secured contains two magnets as 50 and 51. The Hall Effect switch 52 is rigidly positioned so that each time a magnet passes the device, a series of pulses are produced. Thus, in the timing diagram shown magnet 51 is represented by pulse A, while magnet 50 is represented by pulse B. As can be seen during each revolution of the platform 22, the Hall Effect switch 52 responds to the magnetic field of magnets 50 and 51 to provide the timing signal as shown. The signals from the Hall Effect sensor 52 is directed to the trigger input of a flip flop 100. The flip flop takes the pulse train and produces a uniform amplitude pulse train therefrom. This signal is applied to one input of a phase comparator 101. The other input to the phase comparator is obtained from a crystal oscillator 102 whose output is divided by a factor N through frequency divider 103. The output from the phase comparator is coupled via an amplifier 104 to the motor 26 which in turn controls the speed of the platform 22.

Essentially, the above described circuitry constitutes a phase locked loop, many examples of which are well known. The feedback error signal from the phase comparator 101 keeps the rotational speed of the motor 26 in exact synchronization with the frequency of the crystal oscillator. The pulse train from the Hall Effect sensor is also applied to one input of AND gates 110, 111, and to a delay circuit 112 which may be a RC delay. By knowing the angular velocity of the rotating mirror as controlled, the system will produce transmit signals so that the resulting scan lines are evenly spaced. In addition, the scan lines must be reproduceable from frame to frame as the eye is very sensitive to small changes in an image element position. These changes, if not controllable, will produce shimmer of the display. To establish the reproducibility, the system employs two magnets as described one for each of the two scanning sides of the rotating mirror. Rather than depending upon mechanical accuracy to produce repeatability on each line scan, the magnets as 50 and 51 are offset from the diameter of the plateform 23 by the angle $\phi$. The resulting Hall Effect sensor signals are similarly offset in time. This offset is detected by the use of a one-shot multivibrator 113. The multivibrator 113 detects the asymmetry of the pulses as it has a time period which is set for one half the pulse period. The gate 114 prevents the multivibrator 113 from triggering during the set interval.

In this manner the output of the one-shot 113 enables either gate 110 or 111 which thereby determines which side of the rotating mirror is scanning the beam, as for example the A or B side of the mirror. Once this is known, the start frame pulse can be properly delayed via a variable delay circuit 115. This delay is implemented for each side of the rotating mirror which therefore operates to compensate for unintentional mechanical offsets as well as for built in offsets. Therefore, by adjusting the delay one can eliminate any flicker in the image while maintaining interchangeability between different scan heads.

In view of the above description, it is seen that the main aspect of this invention is the use of a multi-surface rotatable mirror. In the Preferred Embodiment the mirror is of a tent shaped configuration, and based on rotation, the scan head approximates a desired scan plane since the rotation of the mirror is in one direction, and because the mirror runs at constant speed, the system eliminates the start-stop pertubations which exist in most oscillating scanners. The system is easy to operate and provides a display which can be used by those skilled in dealing with conventional ultrasonic displays.

We claim:

1. An ultrasonic scanner apparatus for directing ultrasonic energy towards a body under investigation such as the body of a person, for producing scan image data indicative of the interior of said person's body, comprising;

a focussed ultrasonic transducer means for radiating a beam of ultrasonic energy in a given direction, a rotating reflector having at least two different surfaces each of which intercepts a portion of said beam to reflect said intercepted energy in opposite directions said reflector rotating about an axis whereby said unidirectional rotation is manifested by no translational movement, means responsive to one of said reflected beams for scanning the said body under investigation whereby image data of the interior of said body as scanned is provided.

2. The ultrasonic scanner apparatus according to claim 1, wherein said ultrasonic transducer is a disc transducer.

3. The ultrasonic scanner apparatus according to claim 2, wherein said rotating reflector is a solid triangular reflector of a "tent" like configuration having first and second reflecting sides directed from a common apex with said apex positioned in a plane defined by the diameter line of said disc transducer and the transmission axis intersecting the same.

4. The ultrasonic scanner apparatus according to claim 3 further including a fixed reflector positioned at an angle corresponding to the base angle of said rotating reflector and operative to direct intercepted ultrasonic waves in a direction relatively parallel to the direction of said radiated beam from said transducer.

5. The ultrasonic scanner apparatus according to claim 4 wherein said fixed reflector has a conical reflecting surface.

6. The ultrasonic scanner apparatus according to claim 1, wherein said rotating reflector is a truncated tetrahedron having three reflecting surfaces.

7. The ultrasonic scanner apparatus according to claim 1 further including acoustic absorber means positioned to absorb the energy from said other reflected beam.

8. An ultrasonic scanning apparatus for directing ultrasonic energy towards a body under investigation, comprising;

a housing having an internal hollow cavity, with said cavity filled with a liquid capable of propagating ultrasonic energy, an ultrasonic transducer mounted within said cavity for radiating a beam of ultrasonic energy in a given direction, a unidirectionally rotatable reflector mounted within said cavity and having at least two major reflecting surfaces and positioned to intercept said beam of ultrasonic energy emanating from said transducer, to provide a reflected beam at one of said surfaces, a lens assembly positioned between said transducer and said rotating reflector for directing ultrasonic energy towards said rotating reflector, a fixed reflector positioned with said cavity at an angle with respect to said reflected beam from said rotatable reflector to intercept said beam and reflect said beam from said rotatable mirror relatively parallel to said given direction out of said housing.

9. The ultrasonic scanning apparatus according to claim 8, wherein said rotatable reflector is of a "tent" like configuration having a central apex with first and second sloped reflecting surfaces depending therefrom and having a relatively flat base, with the apex facing said transducer.

10. The ultrasonic scanning apparatus according to claim 9, wherein said transducer is a disc transducer with the apex of said rotatable reflector directed parallel to a diameter of said transducer to cause said reflector to provide two reflected beams each propagating in opposite directions.

11. The ultrasonic scanning apparatus according to claim 9, wherein said rotatable reflector is positioned so that one surface intercepts and reflects energy from said transducer to cause said reflector to provide a single reflected beam.

12. The ultrasonic scanning apparatus according to claim 8, further including an auxiliary lens positioned between said rotatable reflector and said fixed reflector to intercept said reflected beam prior to impingement of the same upon the surface of said fixed reflector.

13. The ultrasonic scanning apparatus according to claim 8, further including an auxiliary lens positioned within said cavity to intercept said beam as it is reflected from said fixed reflector in order to further shape said beam prior to exit of the same from said housing.

14. The ultrasonic scanning apparatus according to claim 9, further including a rotatable platform mounted in said cavity and having the base of said "tent" like reflector secured thereto and driving means coupled to said platform for rotating the same.

15. The ultrasonic scanning apparatus according to claim 14, further including sensing means positioned in said housing and operative to provide a signal indicative of the position of said "tent" reflector as said platform is rotated and control means responsive to said signal for controlling the rotation of said platform via said driving means.

16. The ultrasonic scanning apparatus according to claim 8, further including a selective rotatable turret assembly mounted in said cavity and having positioned thereon a plurality of ultrasonic transducers for selecting any one of said plurality to cause said selected one to radiate said beam of ultrasonic energy.

17. An ultrasonic scanner apparatus for directing ultrasonic energy towards a body under investigation such as the body of a person, for producing scan image data indicative of the interior of said person's body, comprising;

a focussed ultrasonic transducer means for radiating a beam of ultrasonic energy in a given direction, a unidirectional reflector having at least two distinct reflecting surfaces at least one of which intercepts said beam for redirecting the beam in a direction relatively perpendicular to said given direction said reflector rotating about an axis whereby said unidirectional rotation is manifested by no translational movement, and, means responsive to said redirected beam for scanning the said body under investigation whereby image data of the interior of said body as scanned is provided.

18. The ultrasonic scanner apparatus according to claim 17, wherein said rotating reflector is a said triangular reflector of a "tent" like configuration having first and second reflecting sides directed from a common apex facing said transducer.

19. The ultrasonic scanner apparatus according to claim 17, wherein said rotating reflector is a truncated tetrahedron having three distinct reflecting surfaces.

* * * * *